(12) United States Patent
Lee

(10) Patent No.: US 10,507,175 B1
(45) Date of Patent: Dec. 17, 2019

(54) CURLING MASCARA COMPOSITIONS

(71) Applicant: ELC MANAGEMENT LLC, Melville, NY (US)

(72) Inventor: Wilson A. Lee, Hauppauge, NY (US)

(73) Assignee: ELC MANAGEMENT LLC, Melville, NY (US)

( * ) Notice: Subject to any disclaimer, the term of this patent is extended or adjusted under 35 U.S.C. 154(b) by 0 days.

(21) Appl. No.: 16/381,806

(22) Filed: Apr. 11, 2019

(51) Int. Cl.
| | |
|---|---|
| *A61Q 5/06* | (2006.01) |
| *A61K 8/81* | (2006.01) |
| *A61K 8/88* | (2006.01) |
| *A61Q 1/10* | (2006.01) |
| *A61K 8/34* | (2006.01) |

(52) U.S. Cl.
CPC .............. *A61K 8/8152* (2013.01); *A61K 8/88* (2013.01); *A61Q 1/10* (2013.01); *A61K 8/345* (2013.01); *A61K 2800/30* (2013.01); *A61K 2800/43* (2013.01); *A61K 2800/594* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 5,874,072 A | 2/1999 | Alwattari et al. | |
| 7,323,162 B2 | 1/2008 | Martin et al. | |
| 7,682,621 B2 | 3/2010 | Lamberty et al. | |
| 8,932,570 B2 | 1/2015 | Mu et al. | |
| 2010/0247470 A1* | 9/2010 | Friel | A61K 8/06 424/70.7 |
| 2013/0039874 A1* | 2/2013 | Li | A61K 8/8152 424/70.7 |
| 2018/0369119 A1* | 12/2018 | Lee | A61K 8/8152 |

* cited by examiner

*Primary Examiner* — Susan T Tran
(74) *Attorney, Agent, or Firm* — Peter Giancana

(57) ABSTRACT

Mascara compositions that comprise ammonium styrene/acrylate copolymer and acrylates/VA copolymer as a plasticizer, in an aqueous base. In the concentrations specified, herein, the resulting mascara compositions have various useful properties that can be controlled, such as transition temperature, viscosity, dry time and degree of contraction. Compositions of the invention are hydrophilic. Nevertheless, after application, the compositions dry to a contracted hydrophobic state that retains curl. The applied composition resists transfer, smudging, flaking, humidity, oil and sebum, making them very suitable as 24 hour long wear cosmetics. Some preferred embodiments comprise an unusually high concentration of nylon fibers, which enhances volume and lengthening of eyelashes.

5 Claims, No Drawings

CURLING MASCARA COMPOSITIONS

FIELD OF THE INVENTION

The present invention is in the field of cosmetics, specifically high-shine mascara compositions that are able to curl the eyelashes.

BACKGROUND

The look conferred by a high gloss (high shine) color cosmetic product is considered glamorous and sensual. However, high shine products have tended to have little staying power on the skin or hair. Flaking and smudging are common problems with high shine products. To reduce flaking and smudging, measures may be taken that would not be necessary for non-glossy mascara products. One such measure has been the use of film forming agents in the mascara composition. Such materials provide a certain level of gloss and staying power, but that gloss is proportional to the amount of film former used. If too much film former is needed to achieve a level of gloss, then the product will be hard, which makes it subject to cracking, and difficult to remove with water alone.

Film forming systems may also be useful for imparting curl the eyelashes, especially if the film contracts as it dries. In such systems, the types and amounts of film formers must selected to provide just the right amount of contractile force and dry time. Too little contraction force and a short dry time means that the eyelashes will curl little or not at all, and too much contraction force and a long dry time will result in an undesirable, unnatural look. Thus, a high gloss mascara that also curls the eyelashes is even more difficult to formulate.

Another issue in film-forming systems is that there tends to be a loss of color intensity, true color and/or shine as the solvent evaporates (that is, the composition does not "wear" well).

Thus, achieving a high-shine, true-color mascara composition that provides the right amount of curl to the eyelashes, while avoiding stability issues, such as syneresis, has not been a simple task. This challenge is further exacerbated by other consumer product demands that must be addressed, such as easy removal from the eyelashes. To date, satisfactory results have not been achieved. There is, therefore, still a need for mascara compositions that meet these, and other, consumer demands. It will be especially advantageous to provide high gloss, long wear mascara compositions that curl and lengthen the eyelashes, and provide true color, while exhibiting reduced flaking and smudging. The present invention provides such compositions.

Conventional mascara formulations include oil-in-water emulsion mascaras which may typically have an oil phase to water ratio of 1:7 to 1:3. Generally, oil-in-water mascaras do not stand up well to exposure of water and humidity. There are also water-in-oil mascaras whose principle benefit is water resistance and long wearability, but generally suffer from difficulty in removing the product from the lashes, and a long dry-time.

In contrast, co-pending application, U.S. Ser. No. 15/632,903, discloses high shine color cosmetic compositions that are flexible, smudge and flake resistant, as well as oil resistant, making them very suitable as high shine, long wear cosmetics. These compositions are initially hydrophilic, but dry hydrophobic. The compositions comprise specific combinations of acrylates/VA copolymer and acrylates copolymer in a cosmetically acceptable base or delivery vehicle, and are suitable as mascara products. However, this application fails to disclose compositions comprising 10% to 30% of ammonium styrene/acrylate copolymer and 1% to 6% of acrylates/VA copolymer as a plasticizer, as disclosed herein, and the benefits thereof, as described for the first time, herein.

SUMMARY

The present invention relates to mascara compositions that comprise ammonium styrene/acrylate copolymer and acrylates/VA copolymer as a plasticizer, in an aqueous base. In the concentrations specified, herein, the resulting mascara compositions have various useful properties that can be controlled, such as transition temperature, viscosity, dry time and degree of contraction. Compositions of the invention are hydrophilic. Nevertheless, after application, the compositions contract, which imparts curl, until fully dry in a relatively stiffer state that retains the imparted curl, resists transfer, smudging, flaking, humidity, oil and sebum, making them very suitable as 24 hour long wear cosmetics. Some preferred embodiments comprise nylon fibers, which enhance volume and lengthening of eyelashes.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All percentages are by weight of the final composition, unless otherwise specified.

Throughout the present specification, "film former" or the like refers to a polymer leaves a film on the substrate to which it is applied, for example, after a solvent accompanying the film former has evaporated, absorbed into and/or dissipated on the substrate.

"Curl" refers to the degree to which a mascara product causes bending of a treated eyelash (upward bend of upper eyelashes, downward bend of lower eyelashes) relative to the untreated lashes. "Length" is the dimension of the lash from the free tip to its point of insertion in the skin. "Flaking" refers to pieces of mascara coming off the lashes after defined hours of wear. "Smudging" is the propensity for mascara to smear after defined hours of wear, when contacting the skin or other surface. Smudging is facilitated by the mascara mixing with moisture and/or oil from the skin or environment. Flaking and smudging are undesirable qualities of a mascara composition, while curl and lengthening are often desirable.

"Transfer resistant" means that compositions of the invention are not readily removed by incidental contact with another material, such as clothing or water. Transfer resistance may be evaluated by any method known in the art. For example, a composition may be evaluated based on the amount of product transferred from the skin or hair of a wearer to any other substrate, such as clothing. For example, a composition may be transfer resistant if a majority of the product is left on the wearer's skin or hair. Further, the amount transferred may be compared with that transferred by other compositions, such as commercially available compositions. In preferred embodiments of the present invention, little or no composition is transferred from the skin or hair to another substrate.

"True color" compositions are those in which the color of the applied composition, after a period of time, remains the same or substantially the same as at the time of application to the skin or hair.

Compositions that maintain color intensity, true color and degree of shine after the solvent evaporates are said to exhibit "good wear" or "long wear".

A "flexible" composition is one that when applied to the skin or hair for its intended use, does not crack or flake for a defined period of time, such as four hours or eight hours of wear. If a composition is not adequately flexible, then it is "rigid".

"Water resistant" means that a composition deposited on the skin or hair, after it has been allowed to dry or cure, does not dissolve or re-wet or absorb moisture or be otherwise adversely affected by the water to a significant degree.

By "single phase" it is intended that the composition is in a stable homogeneous form rather than in the form of a heterogeneous water-in-oil or oil-in-water emulsion.

"Comprising" and the like, mean that a list of elements may not be limited to those explicitly recited.

Ammonium Styrene/Acrylates Copolymer

A first main ingredient of the invention is ammonium styrene/acrylates copolymer (2-Propenoic acid, polymer with ethenylbenzene, ammonium salt), which is the ammonium salt of a polymer of styrene and a monomer consisting of acrylic acid or methacrylic acid. In the present invention, a film of ammonium styrene/acrylates copolymer provides the contractile force that curls the eyelashes as it dries.

Compositions of the invention typically comprise about 10% to about 30% of ammonium styrene/acrylates copolymer by total weight of the composition, for example 10% to 25%, 10% to 20%, 10% to 15%, 15% to 30% 15% to 25%, 15% to 20%, 20% to 30%, 20% to 25%, 25% to 30%, or 11.25% to 27% by total weight of the composition. Greater than about 30% will make the compositions too stiff. Preferred, is 10% to 25%, more preferred is 15% to 20%.

Ammonium styrene/acrylates copolymers having various glass transition temperatures are commercially available. In the present invention, these may be used individually or in combination. Preferred is a combination of exactly two ammonium styrene/acrylates copolymers whose glass transition temperatures are in a ratio of 2:1 to 3:1, and both are no greater than 35° C. When ratio of larger $T_g$ to smaller $T_g$ is in the range 2:1 to 3:1, then the relative concentration of the larger $T_g$ polymer to smaller $T_g$ polymer will be about 1:1 to 4:1. For ratios of $T_g$ outside of 2:1 to 3:1, different relative concentrations of two ammonium styrene/acrylates copolymers can be arrived at by trial and error.

As an example, Vinysol 1012JC and Vinysol 1013JH from Daido Chemical Corp. may be useful. Vinysol 1012JC and Vinysol 1013JH are 45.0% aqueous mixtures of ammonium styrene/acrylates copolymer. Vinysol 1012JC and Vinysol 1013JH are reported to be anionic, have a pH between 6.5 and 9.0, and a viscosity between 5 and 500 mPa-s, The calculated glass transition temperature ($T_g$) of Vinysol 1012JC is reported to be 15° C., while that of Vinysol 1013JH is reported to be 30° C. A higher $T_g$ means that the film will be stiffer. Given that the glass transition temperatures of these two polymers are in a ratio of 2:1, the relative concentration of Vinysol 1013JH to Vinysol 1012JC in compositions of the invention will be about 1:1 to 4:1.

As noted, Vinysol 1012JC and Vinysol 1013JH are 45.0% aqueous mixtures of ammonium styrene/acrylates copolymer. Therefore, when using Vinysol 1012JC, Vinysol 1013JH or a combination of the two, in order to achieve the concentrations of ammonium styrene/acrylates copolymer noted above, the total concentration of Vinysol 1012JC and Vinysol 1013JH should be about 22.2% to about 66.7% by total weight of the composition. Preferred is about 22.2% to 55.6%, more preferred is 33.3% to 44.4% most preferred is about 40% by weight of the composition.

Acrylates/VA Copolymer

A second main ingredient of the invention is acrylates/VA copolymer (INCI name), C15H2604, also known as ethenyl acetate or 2-ethylhexyl prop-2-enoate (IUPAC names); CAS number 25067-02-1. For detailed information, see PubChem Compound Database; CID=168269.

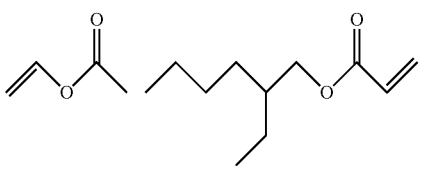

In cosmetics, this material often functions as a binder, film former, adhesive and/or hair fixative. In the present invention, however, we disclose the usefulness of acrylates/VA copolymer as a plasticizer for ammonium styrene/acrylates copolymer. It appears that upon mixing at temperatures disclosed herein, the acrylates/VA copolymer loosens some of the bonds of the ammonium styrene/acrylates copolymer. Without wishing to be bound by theory, perhaps portions of the acrylates/VA copolymer become inserted into the structure of the ammonium styrene/acrylates copolymer, thus lengthening and weakening some of the bonds.

Thus, the degree of curl that composition according to the invention will impart can be controlled by adjusting the ratio of ammonium styrene/acrylates copolymer to acrylates/VA copolymer. Compositions of the invention typically comprise 0.5% to 2.8% of acrylates/VA copolymer by total weight of the composition, for example 0.5% to 2.5%, 0.5% to 2.0%, 0.5% to 1.5%, 0.5% to 1.0%, 1.0% to 2.8%. 1.0% to 2.5%, 1.0% to 2.0%, 1.0% to 1.5%, 1.5% to 2.8%, 1.5% to 2.5%, 1.5% to 2.0%, 2.0% to 2.8%, 2.0% to 2.5%, or 2.5% to 2.8% by total weight of the composition. Acrylates/VA copolymer at concentrations less than about 0.5% is unable to plasticize the ammonium styrene/acrylates copolymer sufficiently, and the resulting composition would contract excessively, causing an unnatural excessive curl of the eyelashes. The composition would also be very brittle, and, therefore, susceptible to flaking. Acrylates/VA copolymer at concentrations greater than about 2.8% will make compositions easier to remove from an application surface, but also render the contractile force of the ammonium styrene/acrylates copolymer to little to effect lash curling, as well as compromise the water resistance of the mascara. The concentrations of ammonium styrene/acrylates copolymer and acrylates/VA copolymer disclosed herein, strike a balance that results in a commercially acceptable mascara composition with excellent performance.

Acrylates/VA copolymer is commercially available, for example, as Vinysol 2140L from Daido Chemical Corp. Vinysol 2140L is reported to have a pH of 4.5, a viscosity of 2,000 mPa-s, a calculated glass transition temperature ($T_g$) of −9° C. Vinysol 2140L is a 46.6% aqueous mixture of acrylates/VA copolymer. Therefore, when using Vinysol 2140L, in order to achieve the concentrations of acrylates/VA copolymer noted above, the concentration of Vinysol 2140L should be about 1% to 6% by total weight of the composition.

Form of Composition and Other Ingredients

Preferred compositions of the invention are a single aqueous phase, and have no gels, waxes, oils or silicones.

Pigments are optional. For a clear coating that imparts shine and curl with no additional color, there will be no pigment in the composition. On the other hand, for color-imparting compositions of the invention, the composition will typically comprise up to 10% of pigments Compositions of the invention should comprise at least 50% of water by weight of the total composition. This amount of water is that from all sources, such as that in Vinysol 2140L, Vinysol 1012JC and Vinysol 1013JH. One advantageous feature of compositions of the present invention is that they are hydrophilic before and during use, but hydrophobic upon drying, which renders the applied composition waterproof. The ability to formulate in an aqueous, hydrophilic state that dries to a hydrophobic state (while having other beneficial properties described herein) is a great advantage of the present invention. While the composition is in a first or hydrophilic state, the ability to formulate with water soluble ingredients is enhanced, and application of the cosmetic is easier and feels nicer. When dried to a second or hydrophobic state, the applied composition resists breakdown from exposure to moisture.

To achieve sufficient hydrophilicity in the first state, the use of hydrophobic materials should be limited to no more than about 0.5% based on total weight of the composition; preferably no more than 0.25%. Materials that are partly hydrophilic and partly hydrophobic could possibly exceed this limits, based on the performance of the final composition. In some embodiments of the invention, it is preferable if the composition comprises no hydrophobic ingredients, such as hydrophobic oils or waxes. Oils are organic substances that are liquid at ambient temperature, such as esters, triglycerides, hydrocarbons and silicones. A typical wax used in cosmetic compositions is carnauba wax. In some embodiments of the invention, it is most preferable if the compositions contain no hydrophobic oils or waxes. Nevertheless, upon drying to a film, the film clearly exhibits hydrophobicity, making it resistant to water. The composition remains in place, having excellent adhesion to the eyelashes. Furthermore, the composition maintains its high degree of shine, clarity, true color and color intensity, making it an excellent long wear composition.

Various ingredients may be included in the cosmetic compositions to fine tune the consumer experience or enhance the performance of the composition. Alcohols, for example, may be useful to speed up drying after application and/or as preservatives. Amounts of alcohol up to 5% may be useful. The cosmetic compositions may also comprise preservatives as needed, typically up to about 2% by weight of the composition. Also, thickeners, viscosity decreasing agents, and/or pH adjusters may be used as needed to create a consumer acceptable product, typically at levels of less than 1% by weight of the composition. At these levels, the foregoing named ingredients do not seem to adversely affect the cosmetic and commercial properties of the compositions.

Glycols, also known as diols (chemical compounds comprising two hydroxyl groups) are optional, but sometimes useful in the present invention. Glycols, such as 1,3-propanediol, might typically be used in cosmetics to enhance the freeze-thaw stability of the composition. Glycols may also prevent polymerization of acrylates/VA copolymer at low temperatures. The use of glycols should be limited to no more than 4% of total glycols, preferably, no more than 1% of total glycols, more preferably no more than 0.5% of total glycols.

Since emulsion forms are excluded from the present invention, it is preferable for surfactants and emulsifiers to be avoided, or only present incidentally, in trace amounts. If present in the aqueous compositions of the invention, any material which demonstrates emulsifier or surfactant properties will have an HLB of less than 12. Therefore, based on total weight of the composition, it is preferable if the composition comprises no more than 3% of surfactants and/or emulsifiers, more preferably no surfactants or emulsifiers.

Further, to enhance clarity of the dried film, it is preferable if the composition comprises no clay particles or undissolved particulate material of any kind at a level that would interfere with the clarity or shine of the dried cosmetic composition. At a minimum, the concentration of clay particles or undissolved particulate material must be limited to a level that does not prevent a desired level of shine in the dried film. Preferably, compositions of the invention comprise no more than 0.25% of clay particles or undissolved particulate material, more preferably no clay particles or undissolved particulate material. One exception to this rule is nylon fibers. To enhance lengthening of the eyelashes, clear nylon fibers may be included in compositions of the invention up to about 10% by weight of the total composition. In conventional emulsion type mascaras, nylon fibers may be limited to about 2%, because more than this tends to ruin the viscosity and stability of the emulsion. This is unlike the single phase aqueous compositions disclosed herein: clear nylon fibers at concentrations as high as 10% do not ruin the stability, clarity, true color and shine of the dried product.

Agents that significantly interfere with the structure of the dried film may degrade the shine, clarity or color. Therefore, it is preferred if compositions of the invention comprise a total of no more than 1.5% of structuring agents, such as xanthan gum, wax, clay (such as bentonite) or stearic acid. More preferably, compositions of the invention comprise a total of no more than 0.05% of structuring agents. Most preferably, compositions of the invention comprise no structuring agents. A useful exception to this rule is sodium stearate. Unlike many structuring agents, sodium stearate is partly hydrophilic, which makes it suitable for an aqueous system. Although sodium stearate is partly hydrophobic, its use has not appeared to compromise the objectives of the present invention. This makes it especially useful in mascara embodiments of the present invention when a structuring or viscosity agent is needed. Sodium stearate may be included as a structuring agent up to 13% by weight of the total composition. More than this amount seems to interfere with the ability of the ammonium styrene/acrylate copolymer to curl the eyelashes.

The following non-limiting examples illustrate additional embodiments of the invention.

| Ingredient | Example 1 | Example 2 | Example 3 | Example 4 |
|---|---|---|---|---|
| | % Concentration | | | |
| [1]Vinysol 2140L | 2.0 | 2.5 | 2.5 | 2.5 |
| [2]Vinysol 1012JC | 30.0 | 40.0 | — | 10.0 |
| [2]Vinysol 1013JH | — | — | 40.0 | 30.0 |
| xanthan gum | 0.9 | 1.11 | 1.11 | 1.11 |
| nylon-6 fibers | 5.0 | 10.0 | 10.0 | 10.0 |
| [3]Distinctive ® Ink Black Chip AQ | 3.9 | 3.9 | 3.9 | 3.9 |
| phenoxyethanol | 0.83 | 0.8 | 0.8 | 0.8 |
| chloroxylenol | 0.2 | 0.2 | 0.2 | 0.2 |
| SD alcohol | 3.5 | 3.5 | 3.5 | 3.5 |
| propanediol | 2.0 | 3.0 | 3.0 | 3.0 |
| water | Q.S. | Q.S. | Q.S. | Q.S. |

[1]46.6% aqueous mixture of acrylates/VA copolymer.
[2]45.0% aqueous mixture of ammonium styrene/acrylates copolymer.
[3]Black 2 (and) Polyester-5 (and) PVP (and) Laureth-4 (40% carbon black).

A preferred procedure for preparing mascara compositions according to the present invention is as follows.
1. In a vessel at room temperature, mix and dissolve the ammonium styrene/acrylates copolymer and acrylates/VA copolymer in a portion of water (this step may be omitted when working with these materials already supplied solution; i.e Vinysol 1012JC, Vinysol 1013JH and Vinysol 2140L).
2. Stepwise, add the remaining ingredients, mixing well to achieve a uniform mass.
3. Allow to cool to approximately 40° C.
4. Pour the composition into packaging.
5. Allow to cool to ambient temperature.

Note, that if he composition includes sodium stearate, as discussed above, then the sodium stearate will first be mixed with a portion of water and heated to 95° C. Continuing to mix, the sodium stearate is then allowed to cool to 50°. After performing step 1, above, the acrylates solution is added to the sodium stearate, and mixed until uniform. Then continue with steps 2-5, above.

Mascara compositions of the invention produce a film on the eyelashes that contracts as it dries, while still retaining some flexibility. The result is a single phase aqueous mascara that imparts high shine and curl, while resisting transfer, smudging, and flaking. After drying, the applied mascara is waterproof and long wearing.

What is claimed is:

1. A single phase, aqueous mascara composition for curling eyelashes comprising, by total weight of the composition:
   one or more ammonium styrene/acrylates copolymers totaling 10% to 30%, wherein the one or more ammonium styrene/acrylates copolymers comprising exactly two ammonium styrene/acrylates copolymers whose glass transition temperatures are in a ratio of 2:1 to 3:1, and whose relative concentrations are 1:1 to 4:1;
   0.5% to 2.8% of acrylates/VA copolymer;
   up to 10% of pigments; and
   at least 50% of water,
   wherein the composition having no more than 3% of surfactants or emulsifiers.

2. The composition of claim 1 having no more than 0.5% of hydrophobic oils or waxes.

3. The composition of claim 1 having no clay particles or undissolved particulate material.

4. The composition of claim 1 further comprising up to 10% of clear nylon fibers.

5. The composition of claim 1 having no more than 4.0% glycol.

* * * * *